(12) United States Patent
Payyavula et al.

(10) Patent No.: US 11,998,293 B2
(45) Date of Patent: *Jun. 4, 2024

(54) SYSTEMS AND METHODS FOR ENTERING AND EXITING A TELEOPERATIONAL STATE

(71) Applicant: INTUITIVE SURGICAL OPERATIONS, INC., Sunnyvale, CA (US)

(72) Inventors: Govinda Payyavula, Sunnyvale, CA (US); Simon P. Dimaio, San Carlos, CA (US); John William Henrie, Palo Alto, CA (US); Brandon D. Itkowitz, San Jose, CA (US); Anthony M. Jarc, Johns Creek, GA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/061,357

(22) Filed: Dec. 2, 2022

(65) Prior Publication Data

US 2023/0110890 A1 Apr. 13, 2023

Related U.S. Application Data

(63) Continuation of application No. 16/489,799, filed as application No. PCT/US2018/020967 on Mar. 5, 2018, now Pat. No. 11,559,365.

(Continued)

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/74* (2016.02); *B25J 9/1689* (2013.01); *A61B 2017/00216* (2013.01); *A61B 2034/2055* (2016.02)

(58) Field of Classification Search
CPC ................... A61B 34/35; A61B 34/74; A61B 2017/00216; A61B 2034/2055; A61B 2034/741; A61B 34/30; B25J 9/1689
(Continued)

(56) References Cited

U.S. PATENT DOCUMENTS

| 11,559,365 B2 | 1/2023 | Payyavula et al. |
| 2008/0253519 A1 | 10/2008 | Bonfiglio et al. |

(Continued)

FOREIGN PATENT DOCUMENTS

| EP | 2520244 B1 | 3/2016 |
| WO | WO-2015143067 A1 | 9/2015 |
| WO | WO-2018057814 A1 | 3/2018 |

OTHER PUBLICATIONS

International Preliminary Report on Patentability for Application No. PCT/US2018/020967, dated Sep. 25, 2019, 9 pages (ISRG08350/PCT).

(Continued)

*Primary Examiner* — Joseph M Dietrich
*Assistant Examiner* — Michael T. Holtzclaw
(74) *Attorney, Agent, or Firm* — Haynes & Boone, LLP (57) ABSTRACT

A teleoperational medical system includes a teleoperational control system, a teleoperational manipulator configured for operating a medical instrument in a medical environment, and an operator controller. The teleoperational control system includes a processing unit including one or more processors. The processing unit is configured to determine whether a head portion of an operator of the operator (Continued)

controller is directed toward or away from a display region of a display device based on at least one marker on the operator that is configured to remain substantially fixed relative to the head portion of the operator during a movement of the head portion. The processing unit is further configured to, based on a determination that the head portion is directed away from the display region for at least a threshold time period, enter a standby mode such that movement of the operator controller does not provide corresponding movement to the teleoperational manipulator.

18 Claims, 8 Drawing Sheets

Related U.S. Application Data (60) Provisional application No. 62/467,506, filed on Mar. 6, 2017.

(51) Int. Cl.
*B25J 9/16* (2006.01)
*A61B 17/00* (2006.01)
*A61B 34/20* (2016.01)

(58) Field of Classification Search
USPC .......................................................... 606/1
See application file for complete search history.

(56) References Cited

U.S. PATENT DOCUMENTS

| | | |
|---|---|---|
| 2012/0071891 A1 | 3/2012 | Itkowitz et al. |
| 2012/0147328 A1 | 6/2012 | Yahav |
| 2013/0030571 A1 | 1/2013 | Ruiz et al. |
| 2013/0218005 A1 | 8/2013 | Desai et al. |
| 2014/0081455 A1* | 3/2014 | Goldberg ............... A61B 90/98 |
| | | 700/250 |
| 2014/0121834 A1 | 5/2014 | Ogawa et al. |
| 2014/0160004 A1 | 6/2014 | Katz et al. |
| 2015/0018841 A1 | 1/2015 | Seo |
| 2015/0182289 A1 | 7/2015 | Itkowitz et al. |
| 2015/0261293 A1 | 9/2015 | Wilairat et al. |
| 2016/0225192 A1* | 8/2016 | Jones .................... A61B 34/20 |
| 2016/0228204 A1 | 8/2016 | Quaid et al. |
| 2017/0057090 A1 | 3/2017 | Fukuda et al. |
| 2019/0328479 A1 | 10/2019 | Wada et al. |
| 2020/0015918 A1 | 1/2020 | Payyavula et al. |

OTHER PUBLICATIONS

International Search Report and Written Opinion for Application No. PCT/US2018/020967, dated Jun. 25, 2018, 17 pages (ISRG08350/PCT).

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR ENTERING AND EXITING A TELEOPERATIONAL STATE

CROSS-REFERENCE TO RELATED APPLICATIONS

This patent application is a continuation of U.S. patent application Ser. No. 16/489,799, filed Aug. 29, 2019, which is the U.S. national phase of International Application No. PCT/US2018/020967, filed Mar. 5, 2018, which designated the U.S. and claims priority to and benefit of the filing date of U.S. Provisional Patent Application 62/467,506, entitled "Systems and Methods for Entering and Exiting a Teleoperational State," filed Mar. 6, 2017, which are incorporated by reference herein in their entirety.

FIELD

The present disclosure is directed to systems and methods for a teleoperational procedure and more particularly to systems and methods for entering and exiting a teleoperational state.

BACKGROUND

Instruments can be used to manipulate and perform tasks in a work space. Such instruments may be configured to be supported and operated partially or entirely by teleoperational manipulator assemblies. Such instruments and teleoperational manipulator assemblies can be used to perform non-medical and medical procedures. As a specific example, medical tools or medical manipulators can be used to perform minimally invasive medical procedures. As another specific example, industrial tools or industrial manipulators can be used in manufacture or testing. As yet other examples, tools or manipulators can be used in procedures for entertainment, exploration, and various other purposes.

As a specific example for minimally invasive medical techniques, minimally invasive medical techniques are generally intended to reduce the amount of tissue that is damaged during invasive medical procedures, thereby reducing patient recovery time, discomfort, and harmful side effects. Such minimally invasive techniques may be performed through natural orifices in a patient anatomy or through one or more incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments that provide a user with a field of view within the patient anatomy.

Some medical and non-medical instrument (including manipulation instruments, imaging instruments or other sensing instruments, etc.) may be teleoperated or otherwise computer-assisted. When performing teleoperational procedures with remote instrument controllers, safe and reliable mechanisms are desired to determine when the teleoperational instruments should be responsive to operator movement of the remote instrument.

SUMMARY

The embodiments of the invention are summarized by the claims that follow below.

In one embodiment, a teleoperational medical system comprises a teleoperational control system and a teleoperational manipulator configured for operating a medical instrument in a medical environment. The teleoperational medical system also comprises an operator controller in communication with the teleoperational control system. The teleoperational control system includes a processing unit including one or more processors. The processing unit is configured to determine whether an operator of the operator controller has a head portion directed toward a display region of a display device and based on a determination that the operator's head portion is directed toward the display region, initiate an operator following mode in which movement of the operator controller provides a corresponding movement to the teleoperational manipulator.

In another embodiment, a method comprises determining whether a head portion of an operator is directed toward a display region of a display device. Based on a determination that the operator's head portion is directed toward the display region, an operator following mode is initiated in which movement of the operator controller provides a corresponding movement to the teleoperational manipulator.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that includes, or does not include, surgical aspects.

Figure 1:
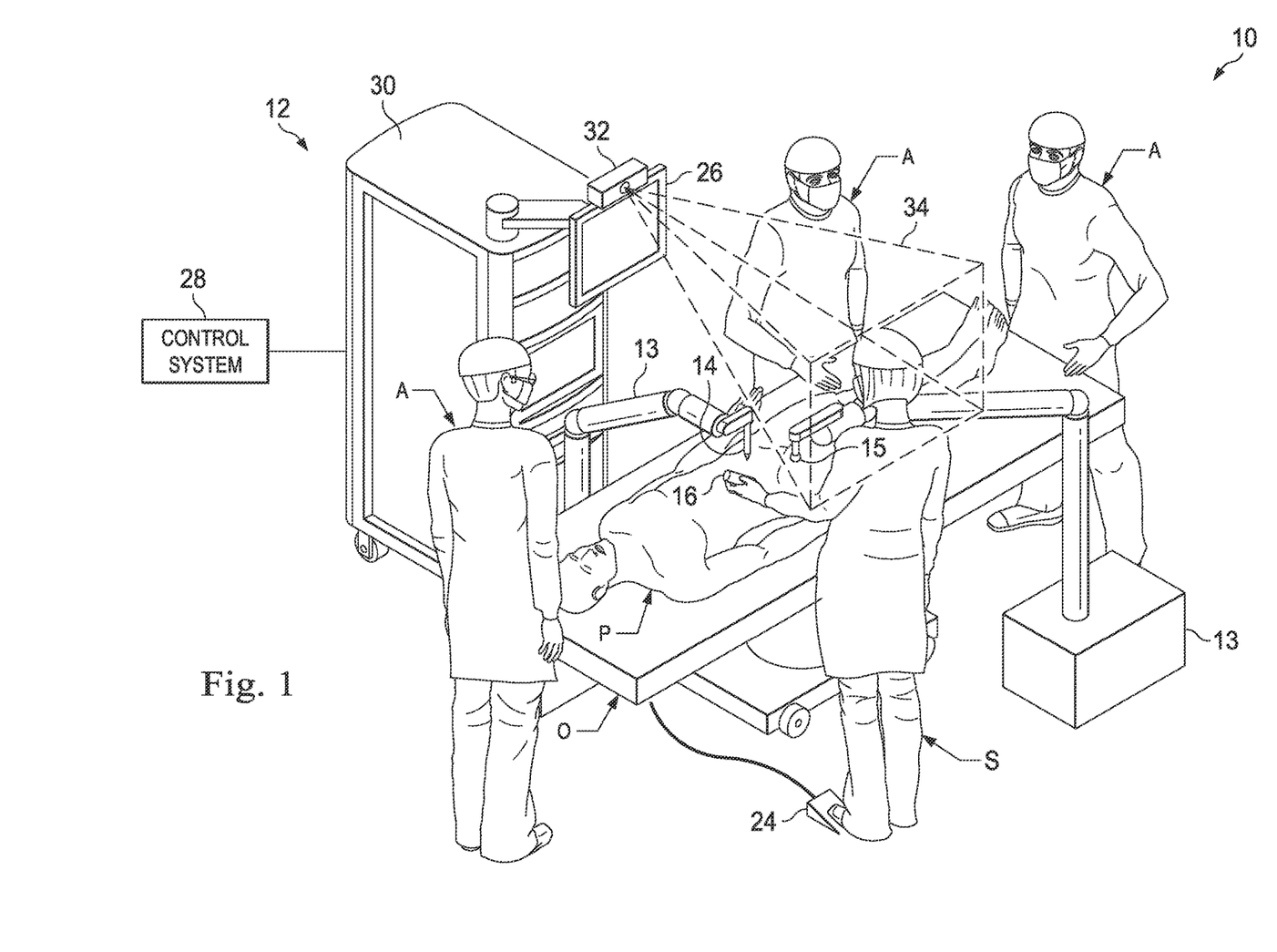
FIG. 1 provides a view of a surgical environment in which a teleoperational medical system operates, in accordance with an embodiment of the present disclosure.

Referring to FIG. 1 of the drawings, a medical environment 10 that includes a teleoperational medical system 12 for use in, for example, medical procedures including diagnostic, therapeutic, or surgical procedures. The teleoperational medical system 12 generally includes a teleoperational assembly 13 mounted to or near an operating table 0 on which a patient P is positioned. For simplicity of explanation, portions of the discussion connected to FIG. 1 will be in connection with a surgical environment implementation of the medical environment 10, and in connection with surgical aspects of the medical procedure. However, the techniques, tools, methods, and apparatuses described in connection with FIG. 1 can also be applied to medical procedures outside of a surgical environment and outside of surgery, or to non-medical procedures outside of any medical environment.

The teleoperational assembly 13 may include one or more modular manipulator arms. A medical instrument system 14 or an endoscopic imaging system 15 may be operably coupled to a teleoperational manipulator (e.g. an arm) of the teleoperational assembly 13. An operator input system 16 allows an operator (e.g. a surgeon, other type of clinician, other type of medical personnel, or other operator) S to control the operation of the medical instrument system 14 and/or the endoscopic imaging system. One or more other persons (e.g. other medical personnel such as assistant surgeons, anesthesiologists, nurses, medical assistants other operators, support personnel) A may also be present in the surgical environment.

For simplicity of explanation, much of this application refers to the operator S as a surgeon, and the person A as an assistant, within the context of a surgical procedure. However, where specialized surgical or assistant skills are not required, the operator S may be a surgeon, some other clinician, some other medical personnel, some non-medical operator, or some other person. Similarly, the person A may be an assistant surgeon, some other clinician, some other medical personnel, some non-medical operator, or some other person. Also, where the procedure performed is not on a patient or is non-medical, (e.g. for an industrial application, for training, for work on a cadaver or anatomy removed from and not to be returned to a patient, etc.), the persons S and A may have little or no medical training or knowledge.

A display system 26 (also called "display 26") may present images captured by the imaging system 15, surgical navigation and guidance images, and/or alphanumeric or symbolic information to assist the surgeon (or other personnel) S or assistants (or other personnel) A with the surgical procedure. The teleoperational medical system 12 also includes a control system 28 in communication with the operator input system 16, the teleoperational assembly 13 and the display system 26, as described below.

Figure 2:
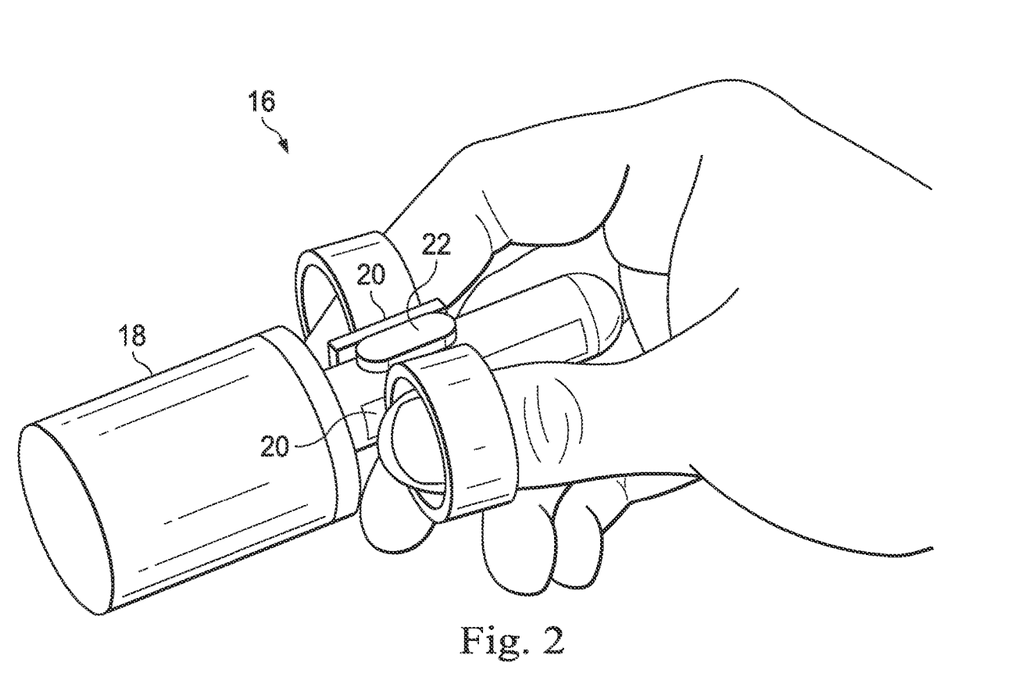
FIG. 2 illustrates an operator controller according to an embodiment of the present disclosure.

In this embodiment, the operator input system 16 includes one or a set of operator hand controllers 18 (FIG. 2) as user input devices for controlling one or multiple medical instrument systems 14 or the endoscopic imaging system 15. The input system also, optionally, includes a pedal control device 24. The operator hand controllers 18 and the pedal control may be located at the side of the patient P. In various alternatives the operator controllers 18 may be tethered by power and/or signal transmission cabling or may be untethered/wireless. In other alternative embodiments, the operator controllers may be located at an operator console such as a surgeon's console, which may be located in the same room as operating table 0. As shown in FIG. 2, the operator controllers 18 may include one or more of any number of a variety of input devices such as grip inputs 20 and trigger switch 22. The input devices may be used to, for example, close grasping jaw end effectors, apply an electrical potential to an electrode, deliver a medicinal treatment, or the like. In various alternatives, the operator input system may additionally or alternatively include joysticks, trackballs, data gloves, trigger-guns, hand or foot-operated controllers, voice recognition devices, touch screens, body motion or presence sensors, and the like. In some embodiments, the hand controllers 18 will be provided with the same degrees of freedom as the medical instruments of the teleoperational assembly to provide the surgeon (or other personnel) with telepresence, the perception that the control device(s) are integral with the instruments so that the surgeon (or other personnel) S has a strong sense of directly controlling instruments as if present at the surgical site. In other embodiments, the hand controllers 18 may have more or fewer degrees of freedom than the associated medical instruments and still provide the surgeon (or other personnel S with telepresence.

The assembly 13 supports and manipulates the medical instrument system 14 while the surgeon (or other personnel) S conducts the procedure from the patient side or another location within the surgical environment. An image of the surgical site within the patient can be obtained by the endoscopic imaging system 15, such as a stereoscopic endoscope, which can be manipulated by the teleoperational assembly 13 to orient the endoscopic imaging system 15. The number of medical instrument systems 14 used at one time will generally depend on the diagnostic or surgical procedure and the space constraints within the operating room among other factors. Each arm of the teleoperational assembly 13 may include a kinematic structure of one or more servo or non-servo controlled links. The teleoperational assembly 13 includes a plurality of motors that drive inputs on the medical instrument system 14. These motors move in response to commands from the control system 28. The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Instruments 14 may include end effectors having a single working member such as a scalpel, a blunt blade, an optical fiber, or an electrode. Other end effectors may include, for example, forceps, graspers, scissors, or clip appliers.

The control system 28 includes at least one memory and at least one processor, and typically a plurality of processors, for effecting control between the medical instrument system 14, the imaging system 15, the operator input system 16, the display system 26, and other auxiliary systems which may include, for example, additional imaging systems, audio systems, fluid delivery systems, display systems, illumination systems, steering control systems, irrigation systems, and/or suction systems. The control system 28 also includes programmed instructions (e.g., a computer-readable medium storing the instructions) to implement some or all of the methods described in accordance with aspects disclosed herein. While control system 28 is shown as a single block in the simplified schematic of FIG. 1, the system may include two or more data processing circuits with one portion of the processing optionally being performed on or adjacent the teleoperational assembly 13, another portion of the processing being performed at the operator input system 16, and the like. In various embodiments, the control system may be housed in an electronics cart 30 to which the display system 26 or other peripheral equipment is mounted. The control system 28 may employ any of a wide variety of centralized or distributed data processing architectures. Similarly, the programmed instructions may be implemented as a number of separate programs or subroutines, or they may be integrated into a number of other aspects of the teleoperational systems described herein. In one embodiment, control system 28 supports wireless communication protocols such as Bluetooth, IrDA, HomeRF, IEEE 802.11, DECT, and Wireless Telemetry.

In some embodiments, control system 28 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 13 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 13. In some embodiments, the servo controller and teleoperational assembly are provided as part of a teleoperational arm positioned adjacent to the patient's body.

The control system 28 can be coupled with the imaging system 15 and can include a processor to process captured images for subsequent display, such as to a surgeon (or other personnel) on a console such as a surgeon's console, or on another suitable display located locally and/or remotely. For example, where a stereoscopic endoscope is used, the control system 28 can process the captured images to present the surgeon (or other personnel) with coordinated stereo images of the surgical site. Such coordination can include alignment between the opposing images and can include adjusting the stereo working distance of the stereoscopic endoscope.

In alternative embodiments, the teleoperational system may include more than one teleoperational assembly and/or more than one operator input system. The exact number of teleoperational assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

During a minimally invasive teleoperational procedure, the surgeon (or other personnel) S may view the surgical site within the patient's body on the display system 26 via images captured by the imaging system 15. The "following mode" of the teleoperational medical system 12 is a system operational state in which the movement of the controllers 18 effect movement of the instruments 14. Generally, when operating the controllers 18 in following mode, the surgeon (or other personnel) S views the images on the display system 26 to carefully control the instruments 14 contacting the patient P. To safely perform a teleoperational procedure, movement of the instruments 14 within the patient anatomy may be suspended when the surgeon (or other personnel) S looks away from the display system or moves to a position inside or outside of the surgical environment in which the display system is not visible. In teleoperational systems where the surgeon operates from a console such as a surgeon's console with a head-in display system, sensors or switches can determine when the surgeon's face is moved away from contact with the console. In patient-side teleoperational systems, the surgeon's head may not be positioned within a console and therefore detecting whether the surgeon is viewing the display system from a distance (e.g. across the operating table 0 or across the room) may be determined by other means. Safety systems described below may be used to determine whether the surgeon (or other personnel) S is viewing the endoscopic images of the surgical site on the display system and may enable or continue an operator following mode when one or more viewing criteria is met.

FIG. 1 illustrates a spatial tracking system 32 that detects objects or markers within a spatial volume 34 of the surgical environment 10. In this embodiment, the spatial tracking system 32 may be an optical tracking system, but in various alternative embodiments, other spatial tracking systems such as acoustic, eye or gaze tracking, electromagnetic, inertial measurement unit (IMU), or hybrid tracking systems may be used. In some embodiments, an optical tracking system may have multiple uses beyond tracking the surgeon's view. For example, the tracking system may also be used for tracking hand motion or for image registration.

In the embodiment of FIG. 1, the tracking system 32 is generally fixed relative to the coordinate frame of the display system 26. For example, the tracking system 32 may be mounted to the display system 26 to track a volume 34 in front of the display. The tracking system 32 may track markers within the volume 34 that indicate whether the surgeon (or other personnel) S, who is spaced a distance apart from the display system 26, is looking at a display region of the display system. In alternative embodiments, the tracking system may be mounted elsewhere in the surgical environment 10 and may use a transformation between the display system position coordinates and the tracking system coordinates to determine the position and orientation of markers or objects relative to the display system. In alternative embodiments, the tracking system may include a camera or other sensor coupled to the surgeon's head which tracks the motion of the surgeon's head and/or eyes relative to static or movable markers with known positions in the surgical environment. In alternative embodiments, the display system may be a virtual display system that has a fixed or known virtual projection plane within the surgical environment. In alternative embodiments, the display system may be a virtual display system projected in a head-mounted augmented reality headset worn by the surgeon (or other personnel) S. The movement of the surgeon's (or other personnel's) head and/or eyes may be tracked using, for example, simultaneous localization and mapping (SLAM) techniques.

Figure 3:
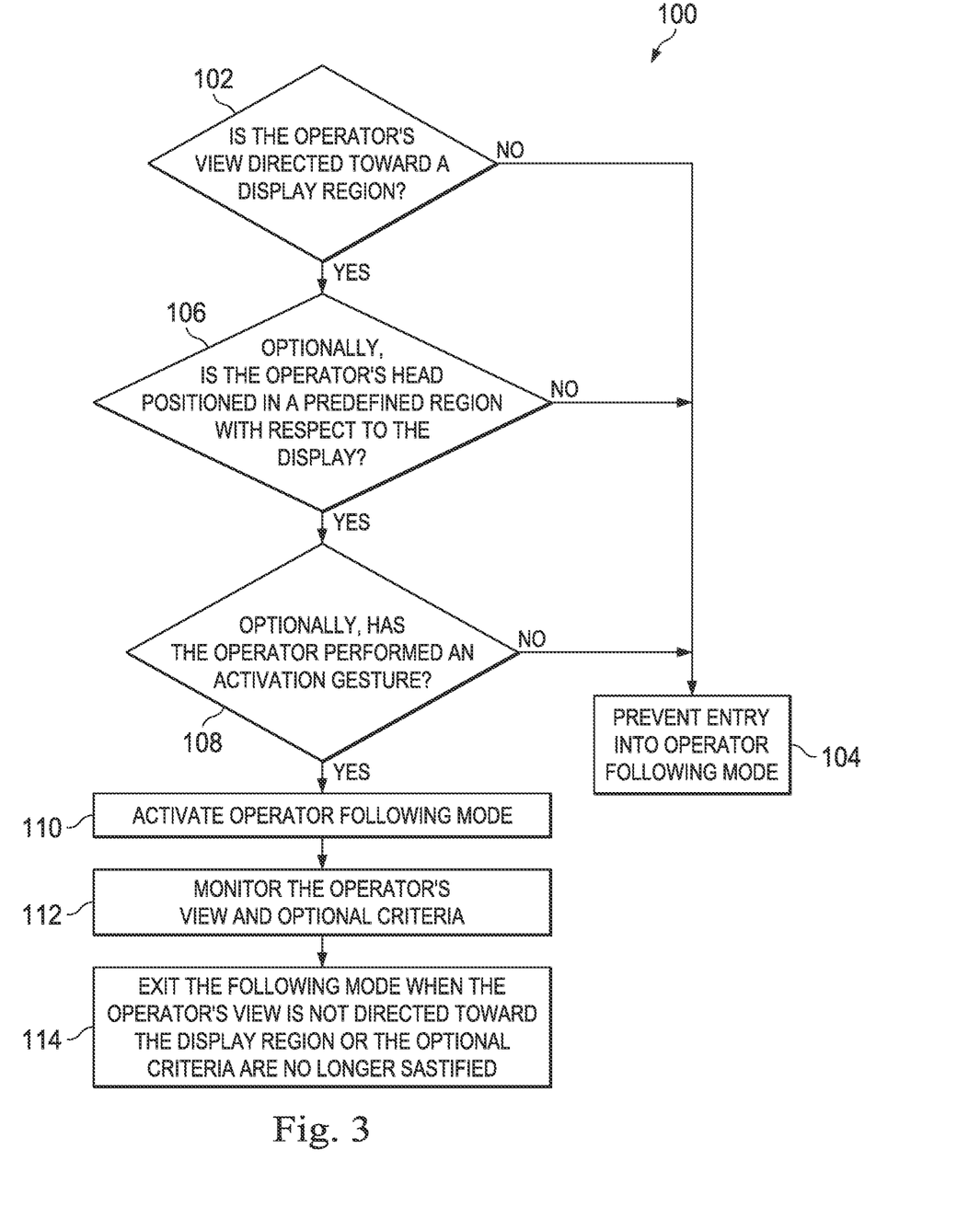
FIG. 3 is a flowchart providing a method for entering an active teleoperational state.

FIG. 3 illustrates a method 100 for entering an active teleoperational state such as an operator following mode of the teleoperational system 12. The method 100 is illustrated in FIG. 3 as a set of operations or processes 102-114. Not all of the illustrated processes 102-114 may be performed in all embodiments of method 100. Additionally, one or more processes that are not expressly illustrated in FIG. 3 may be included before, after, in between, or as part of the processes 102-110. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes.

According to the present example, the method includes a process 102 for determining whether an operator's (e.g. surgeon's or other personnel's) view is directed toward a display region of a display system (e.g. display system 26). This determination may be made, for example, using the tracking system 32. The tracking system 32 may detect markers, including natural landmarks on a portion of the operator's head. Examples of markers tracked by the tracking system 32 are illustrated in FIGS. 4-6.

Figure 4:
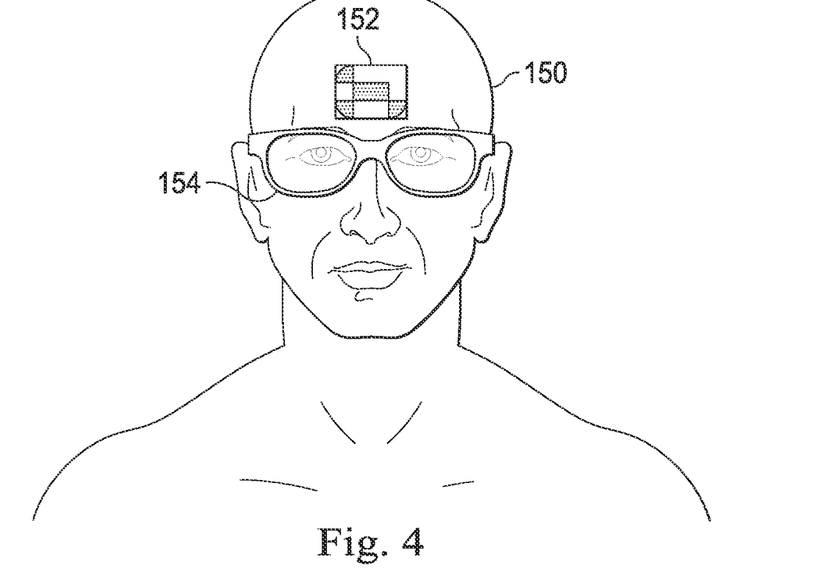
FIGS. 4-6 illustrate optical marker detection systems in accordance with various embodiments of the present disclosure.

FIG. 4 illustrates an operator 150 wearing a marker 152 that may be tracked by the tracking system 32. In this embodiment, the marker 152 is an optical marker that is rigidly coupled to stereo viewing glasses 154 worn by the operator 150. The glasses 154 hold the marker 152 in a generally fixed position relative to the operator's eyes. The position of the operator's eyes relative to the glasses and marker may be measured or known. Based on the known position of the marker 152 relative to the glasses and the known position of the operator's eyes relative to the glasses, the position of the eyes relative to the tracking system 32 may be determined by the tracking system. In this embodiment, the marker is coupled to stereo viewing glasses which the user wears to obtain a 3D view of the images displayed on the display system 26. In alternative embodiments, for example, when glasses are not otherwise used by the operator, the marker may be attached to another accessory coupled to the operator's head such as a head band or an earpiece that may be held generally fixed relative to the operator's eyes. In alternative embodiments, the marker may be attached directly to the operator's head with an adhesive or other coupling device.

Figure 5:
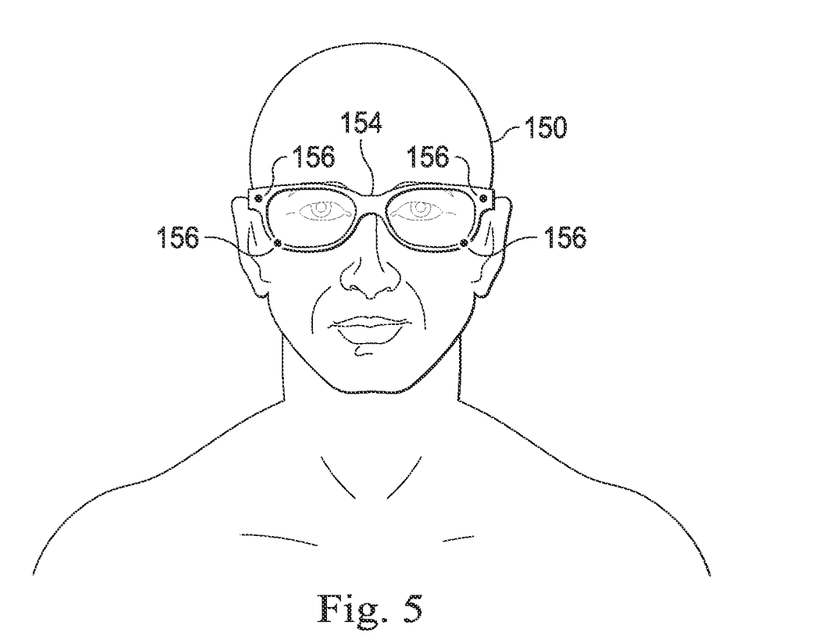

FIG. 5 illustrates the operator 150 wearing a set of one or more optical markers 156 that may be tracked by the tracking system 32. In this embodiment, the markers 156 are rigidly attached to glasses 154 worn by the operator 150. The glasses 154 hold the markers 156 in a generally fixed position relative to the operator's eyes. The position of the operator's eyes relative to the glasses and marker may be measured or known. In this embodiment, the markers 156 frame the operator's eyes, providing a constellation of trackable points that have a generally fixed position relative to the operator's eyes, which allows the position of the eyes to be calculated by the tracking system 32. In various embodiments, ordinary features of the glasses such as corners or the bridge may serve as trackable markers.

Figure 6:
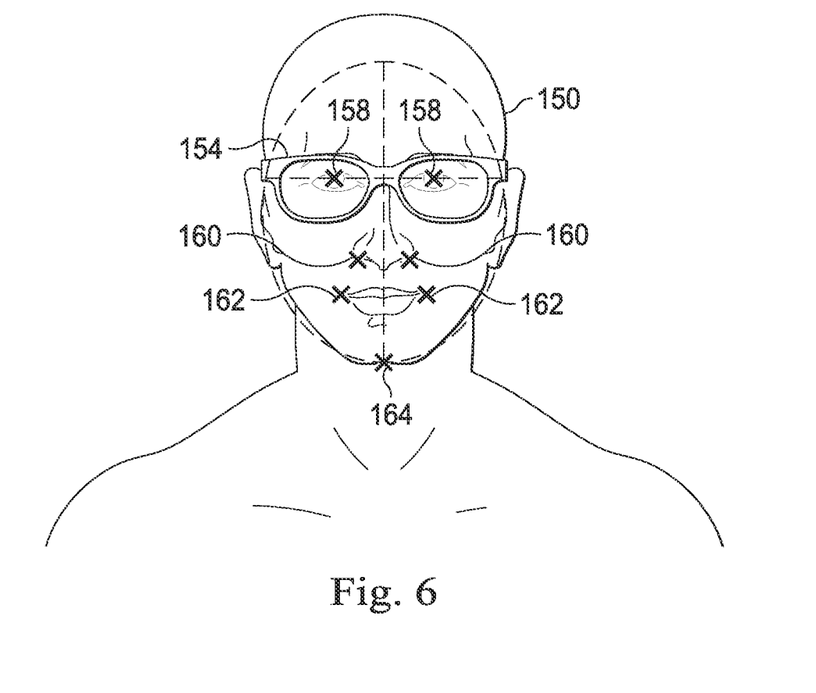

FIG. 6 illustrates natural markers 158-164 corresponding to natural portions of the head of operator 150. These natural markers 158-164 may be tracked by the tracking system 32. For example, natural markers 158 may be the pupils or glint points of the operator's eyes. The natural markers 158 may be used to track the operator's gaze. Natural markers 160 may mark the outer edges of the operator's nose. Natural markers 162 may mark the outer edges of the operator's mouth. Natural marker 164 may correspond to the lowest point of the operator's chin. The natural markers 160-164 may have known positions relative to the operator's eyes. Other markers such as the outline of the operator's face or a derived midline defined between the markers 160, 162, and 164 may also be tracked by the tracking system.

Figure 7:
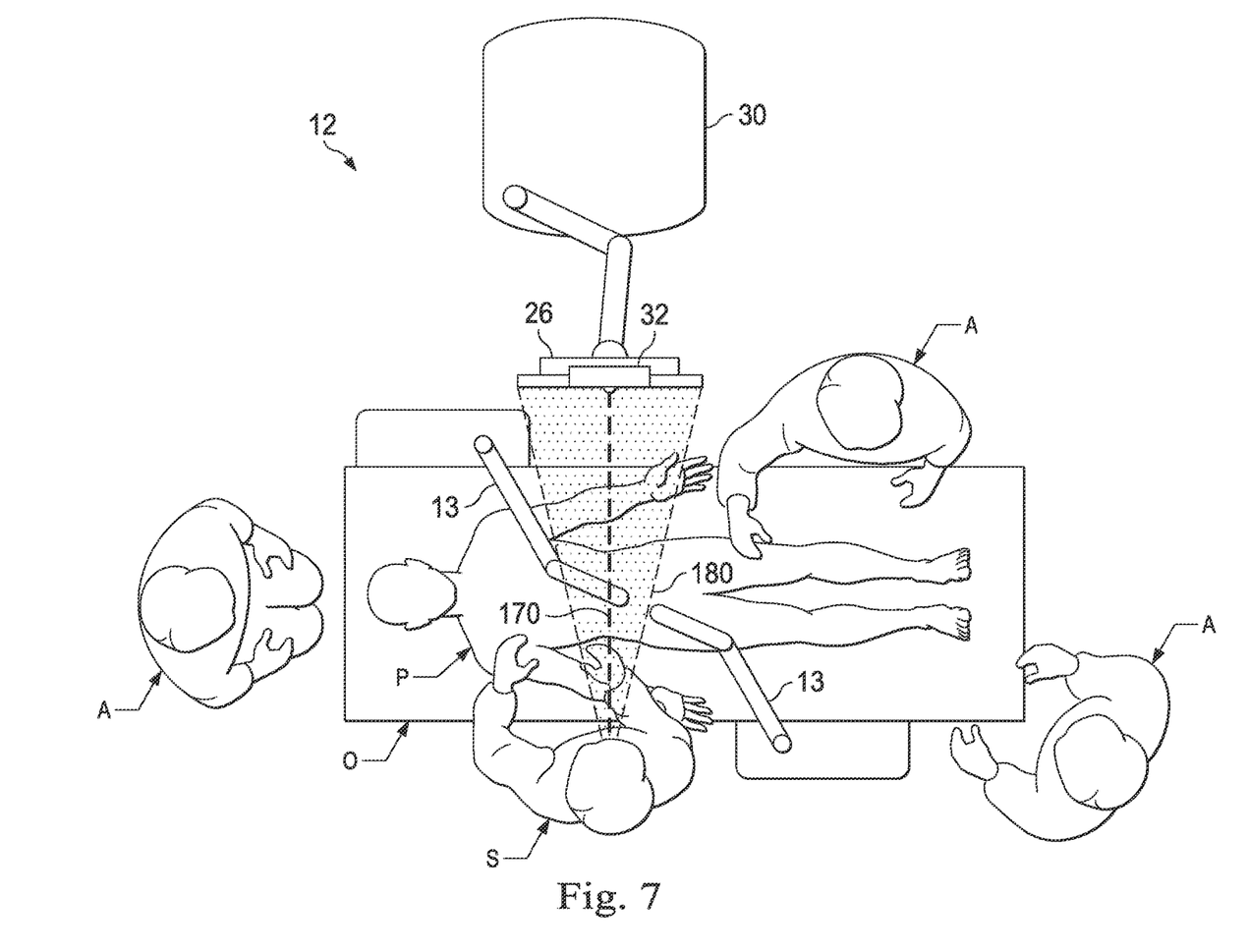
FIGS. 7 and 8 provide overhead views of a surgical environment in which a teleoperational medical system operates, in accordance with an embodiment of the present disclosure.

Referring again to the method 100 of FIG. 3, at process 102 tracking of one or more markers (including natural landmarks or artificial markers) may be used to estimate the position and orientation of the operator's head, face, eyes, gaze, or other head portion. The positions and orientations may be used to compute the looking direction as a viewing vector in the coordinate frame of the display system. FIG. 7 illustrates a viewing vector 170 computed using tracked markers on the surgeon (or other personnel) S. The viewing vector may be, for example, based upon head orientation, eye gaze direction or a combination of the two.

Figure 9:
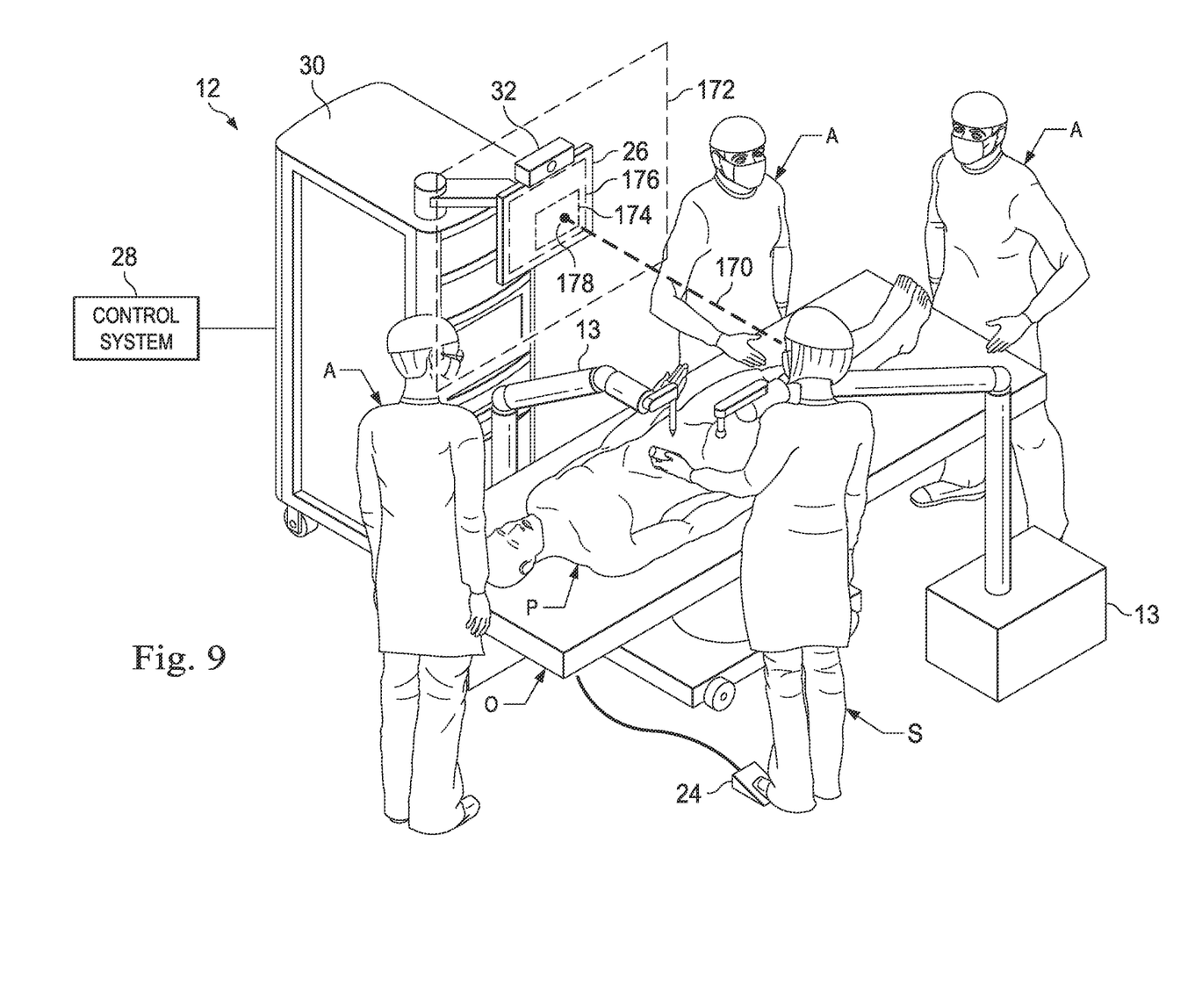
FIG. 9 provides a view of a surgical environment of FIG. 1, and illustrates the intersection of an operator's view vector with a display plane.

FIG. 9 illustrates a display plane 172 which is coincident with the surface of the display system 26. A display region 174 may be smaller than the full display field 176 of the display system 26 viewable by the surgeon (or other personnel) S. The display region 174 may include current endoscopic images or other information critical to the medical procedure. The display plane 172 may include multiple display regions containing different images or information.

At the process 102, to determine whether the operator's view is directed toward the display region 174, an intersection point 178 between the viewing vector 170 and the display plane 172 may be computed. Based on the location of the intersection point 178, the determination can be made as to whether the intersection point 178 is within the boundaries of the display region 174. If the operator's view is within the display region 174, then the operator following mode may be initiated at process 110, allowing the operator's movement of the controllers 18 to translate into movement of the instrument 14. At the process 104, if the operator's view is not directed toward the display region, the entry into following mode is prevented. This serves as a safety mechanism to prevent movement of the instruments 14 within the patient anatomy when the operator looks away from the display region. In alternative embodiments, the determination of the operator's view may be made by computing whether a view angle 180 (FIG. 7) is within permitted bounds of the display region 174 or the display field 176.

Figure 8:
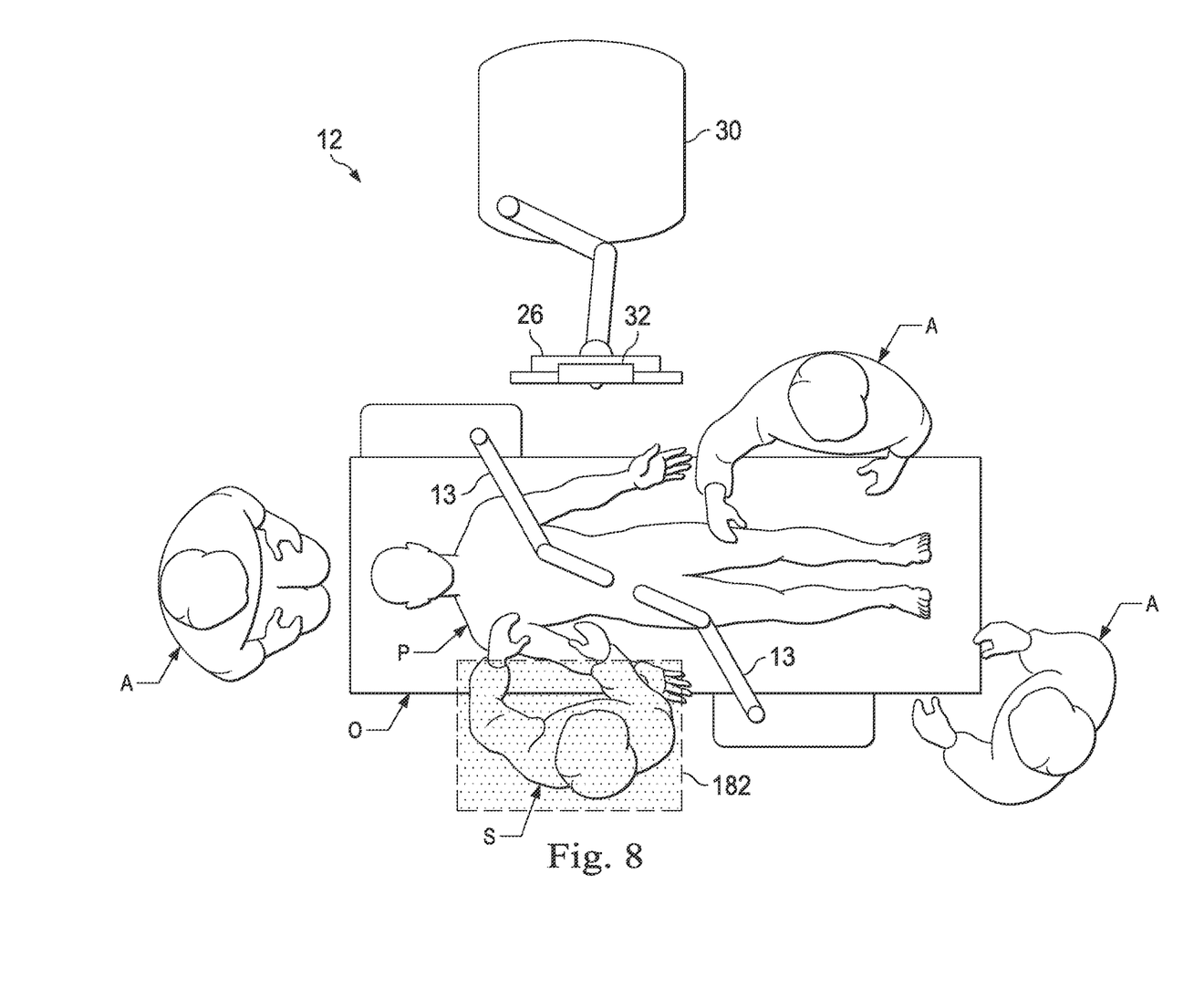

Optionally, transitioning to the operator following mode may be contingent on the evaluation of additional conditions. For example, at optional process 106, the tracking system may determine whether the operator's head is within an operating volume 182 (FIG. 8) located in a predefined position relative to the display system 26. The operating volume 182 may define an acceptable position within the surgical environment 10 from which the procedure may be performed. If the operator is not located within the operating volume, entry into the following mode may be prevented. This also serves as a safety mechanism to prevent movement of the instruments 14 within the patient anatomy when the operator walks away from the accepted location for performing the procedure.

Optionally, transitioning to the operator following mode may be contingent on the evaluation of an activation gesture. For example, at optional process 108, the control system 28 may evaluate whether the surgeon (or other personnel) S has performed an activation gesture. The activation gesture may be, for example, the operator forming a matching grip in which the controller 18 is moved to match the configuration of the instrument 14 visible in the endoscopic image on the display system 26. Matching the configuration may include orienting the controller 18 at the same angle as the instrument and opening or closing the fingers in the grip inputs 20 of the controller to match the jaw spacing of a jawed instrument 14 visible in the display region 174. Other activation gestures may include a hand gesture sensed by the tracking system 32, a pedal movement, button activation, a head gesture, or a verbal command.

Optionally, a variety of other conditions may be required for entering an operator following mode. For example, operator recognition may be required before entering the operator following mode. Operator recognition may be determined using, for example, a facial recognition system, an iris recognition system, a fingerprint recognition system, another biometric identification system, or a voice command. Additionally or alternatively the operator may be required to input identification information or may wear a personal identification marker that may be sensed before entering the following mode. Additionally or alternatively, a presence detector may be used to determine the operator's presence at the controllers 18. The presence detector may be, for example, a capacitive touch sensor.

Another optional criterion before entering the operator following mode at process 110, may be a threshold viewing time period. For example, the operator may be required to maintain the viewing vector or viewing angle for the threshold time period as an indication of intention to perform the procedure and not as an accidental glance.

Referring again to FIG. 3, at a process 112, the surgeon's (or other personnel's) direction of view continues to be monitored by the tracking system 32 throughout the procedure to determine whether the operator's direction of view moves away from the display region 174. As previously described, the operator's direction of view may be determined based on a calculated viewing vector or angle. The optional criteria of operator's head position may also be monitored during the surgical procedure to determine whether the operator moves out of the permitted spatial region. Other optional criteria for maintaining the operator following mode may also be monitored throughout the surgical procedure.

At a process 114, the teleoperational system may exit or suspend the operator following mode if the operator's direction of view moves away from the display region or if any of the optional criteria being monitored are no longer satisfied. The exiting from the following mode may occur immediately upon determination that a criterion is no longer being met. Alternatively, the exiting from the following mode may occur after criterion fails to be met for a predefined threshold period of time. For example, if the operator glances away from the display region for less than the predefined threshold period of time (e.g., 500 milliseconds), the system may remain in following mode. As another example, if the operator glances away from the display region for less than the predefined threshold period of time (e.g., 500 milliseconds), the system may enter a temporary clutched state in which movement of the controllers 18 does not cause movement of the instruments in the patient anatomy while the operator is looking away. That is, if the operator's direction of view moves away and then returns to the display region before the threshold period of time elapses, the system enters into the temporary clutched state when the operator's direction of view has moved away, and then the system exists the temporary clutched state and resumes full following mode when the operator's direction of view has returned. But, if the operator looks away from the display region for a time period that exceeds the predefined threshold time period, the system may terminate following mode so that movement of the controllers 18 no longer causes movement of the instruments in the patient anatomy while the operator is looking away. When following mode is terminated, the system may transition into a standby state or to a master clutch state. To return to the following mode after termination, the operator may reengage with an activation gesture.

To enter a master clutch state, the user begins in following mode. With user inputs such gestures or hand or foot pedal activation, the user may enter into clutch mode. In clutch mode, the teleoperational instrument or endo scope doesn't move while the teleoperational controllers are moving. When teleoperational controllers are moved, the clutch state will allow the user to reset hand position or pause briefly for any reason while still looking at surgical video. The clutch mode may put the system back into following mode without performing an activation gesture. Standby mode is similar to a clutch mode, but the user may enter a standby mode without performing active gestures. Instead a user may enter standby mode if he or she is not looking at an active region of the display for more than a predefined time. When in standby mode, the user may return to following mode by looking into the active region or may exit following mode when not looking at the active region for more than a predefined time. When the system enters standby mode, the teleoperational instruments do not follow the movement of the teleoperational controllers, as in clutch mode.

Optionally, the display may include multiple display regions, with each display region having a different predefined time period for determining suspension of the following mode. In various embodiments, one or more "safe" regions may be established in or out of the display plane such that when the view direction moves to the safe regions a different, longer predefined time period governs suspension of the following mode. Such safe regions may be established, for example, in the viewing direction of the patient anatomy so that the operator may look down at the patient surface for a time period greater than the predefined time period, without the teleoperational system exiting the following mode. Optionally, exiting of the following mode may be accompanied by a visual (e.g. flashing light) or audio (e.g. an audible tone) indicator.

Alternatively, the exiting from the following mode may occur based on a distance between display region and the direction of the operator's view. For example, the time to exit the following mode may be shorter if the operator's view vector intersects the display plane far away from the display region (indicating the operator has looked far away from the display region), and the transition out of following mode may occur after a longer period of time if the view vector intersects the display plane at a location just barely outside of the display region (indicating that the operator may just be looking at other relevant information on the display system.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A teleoperational medical system comprising:
   a teleoperational control system;
   a teleoperational manipulator configured for operating a medical instrument in a medical environment; and
   an operator controller in communication with the teleoperational control system, wherein the teleoperational control system includes a processing unit including one or more processors, and wherein the processing unit is configured to:
   determine whether a head portion of an operator of the operator controller is directed toward or away from a display region of a display device based on at least one marker on the operator, wherein the at least one marker is configured to remain substantially fixed relative to the head portion of the operator during a movement of the head portion; and
   based on a determination that the head portion is directed away from the display region for at least a threshold time period, enter a standby mode such that movement of the operator controller does not provide corresponding movement to the teleoperational manipulator.

2. The teleoperational medical system of claim 1, wherein the processing unit is configured to prevent initiation of an operator following mode responsive to a determination that the head portion is not directed toward the display region.

3. The teleoperational medical system of claim 1, wherein the processing unit is configured to prevent initiation of an operator following mode responsive to a determination that the operator is not present at the operator controller.

4. The teleoperational medical system of claim 1, wherein the at least one marker includes a natural landmark on a face of the operator.

5. The teleoperational medical system of claim 1, wherein the processing unit is further configured to:
   determine whether the head portion is positioned in a predefined region in the medical environments; and
   initiate an operator following mode based on a determination that the head portion is positioned in the predefined region.

6. The teleoperational medical system of claim 1, wherein the processing unit is further configured to:
   determine whether the operator has performed an activation gesture; and
   initiate an operator following mode based on a determination that the operator has performed the activation gesture.

7. The teleoperational medical system of claim 6, wherein the activation gesture is a matching hand grip, that matches a displayed configuration of the medical instrument on the display device, or a movement of a pedal device.

8. The teleoperational medical system of claim 1, wherein the processing unit is further configured to:
   identify the operator; and initiate an operator following mode based on a determination that the identified operator is permitted to operate the teleoperational medical system.

9. The teleoperational medical system of claim 1, wherein the threshold time period is a first threshold time period for a first direction that the head portion is directed away from the display region, wherein the threshold time period is a second threshold time period for a second direction that the head portion is directed away from the display region, wherein the first threshold time period differs from the second threshold time period, and wherein the first direction differs from the second direction.

10. The teleoperational medical system of claim 1, wherein determining whether the operator of the operator controller has the head portion directed toward or away from the display region of the display device includes determining an operator viewing vector and determining whether the operator viewing vector intersects a display plane within the display region.

11. The teleoperational medical system of claim 1, wherein the at least one marker comprises, or is coupled to, an item worn by the operator, the item selected from the group consisting of: glasses, a headband, and an earpiece.

12. The teleoperational medical system of claim 1, wherein the processing unit is further configured to:
determine that the head portion has been directed away from the display region of the display device for less than the threshold time period and has returned to be directed toward the display region; and
remain in an operator following mode based on the determination that the head portion has been directed away from the display region for less than the threshold time period.

13. A method for operating a teleoperational system including a teleoperational manipulator and an operator controller, the method comprising:
determining whether a head portion of an operator is directed toward or away from a display region of a display device based on at least one marker on the operator, wherein the at least one marker remains substantially fixed relative to the head portion of the operator during a movement of the head portion; and
based on a determination that the head portion is directed away from the display region for at least a threshold period of time, enter a standby mode such that movement of the operator controller does not provide corresponding movement to the teleoperational manipulator.

14. The method of claim 13, further comprising:
preventing initiation of an operator following mode responsive to a determination that the head portion is not directed toward the display region or that the operator is not present at the operator controller.

15. The method of claim 13, further comprising:
determining whether the head portion is positioned in a predefined region; and
initiating an operator following mode based on a determination that the head portion is positioned in the predefined region.

16. The method of claim 13, further comprising:
determining whether the operator has performed an activation gesture; and
initiating an operator following mode based on a determination that the operator has performed the activation gesture.

17. The method of claim 13, further comprising:
determining that the head portion has been directed away from the display region of the display device for less than the threshold period of time and has returned to be directed toward the display region; and
remaining in an operator following mode based on the determination that the head portion has been directed away from the display region for less than the threshold period of time.

18. A non-transitory machine-readable medium comprising a plurality of machine-readable instructions which when executed by one or more processors associated with a medical device are adapted to cause the one or more processors to perform a method comprising:
determining whether a head portion of an operator is directed toward or away from a display region of a display device based on at least one marker on the operator, wherein the at least one marker remains substantially fixed relative to the head portion of the operator during a movement of the head portion; and
based on a determination that the head portion is directed away from the display region for at least a threshold period of time, enter a standby mode such that the movement of an operator controller does not provide corresponding movement to a teleoperational manipulator.

* * * * *